United States Patent [19]

Larsen et al.

[11] 4,377,583
[45] Mar. 22, 1983

[54] N-METHYL-D-GLUCAMINE SALT OF WITH 3,4-DIHYDRO-5-METHYL-6-(2-METHYL-PROPYL)-4-OXOTHIENO[2,3-D]PYRIMI-DINE-2-CARBOXYLIC ACID

[75] Inventors: Aubrey A. Larsen; Donald A. Owens, both of Evansville, Ind.

[73] Assignee: Mead Johnson & Company, Evansville, Ind.

[21] Appl. No.: 294,962

[22] Filed: Aug. 21, 1981

[51] Int. Cl.$^3$ .................. C07D 513/04; A61K 31/505
[52] U.S. Cl. .................................... 424/251; 544/278
[58] Field of Search ........................ 544/278; 424/251

[56] References Cited

U.S. PATENT DOCUMENTS 4,054,656  10/1977  Temple ............................ 424/251
4,159,377   6/1979  Temple ............................ 544/278

OTHER PUBLICATIONS

Merck Index, 9th Ed., pp. 792–793, 5945, (1976).

Primary Examiner—Donald G. Daus
Assistant Examiner—S. Gibson
Attorney, Agent, or Firm—Richard P. Ryan; Robert H. Uloth

[57] ABSTRACT

Treatment of the antiallergic agent 3,4-dihydro-5-methyl-6-(2-methylpropyl)-4-oxothieno[2,3-d]pyrimidine-2-carboxylic acid with N-methyl-D-glucamine gives a salt with improved solubility. Solutions of this salt have pH values in a range acceptable for topical formulations. Additionally, solutions of the subject salt exhibit good stability which can be demonstrated by retention of potency. The salt is comprised of a 1:1 molecular ratio of the glucamine base to the acid.

4 Claims, No Drawings

N-METHYL-D-GLUCAMINE SALT OF WITH 3,4-DIHYDRO-5-METHYL-6-(2-METHYL-PROPYL)-4-OXOTHIENO[2,3-D]PYRIMIDINE-2-CARBOXYLIC ACID

BACKGROUND OF THE INVENTION

This invention covers the acid addition salt of 3,4-dihydro5-methyl-6-(2-methylpropyl)-4-oxothieno[2,3-d]pyrimidine-2-carboxylic acid with N-methyl-D-glucamine containing a base to acid molecular ratio of 1:1. The compound of this invention is classified in general as a drug, bio-affecting and body-treating type of compound. The acid component of the subject salt is referred to herein by code number MJ 12175 and is represented by the following structural formula.

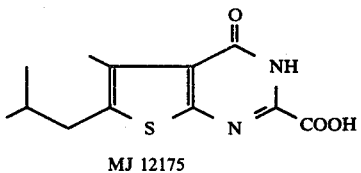

MJ 12175

D. L. Temple, Jr., U.S. Pat. Nos. 4,054,656 and 4,159,377 describe preparation of MJ 12175, its use as an antiallergic agent, and the potassium salt thereof. The latter is advantageous because of its improved water solubility, but solutions thereof are not desirable for nasal instillation because of their alkaline pH. As stated therein, MJ 12175 may be used for antiallergenic purposes in the form of the acid or its metal salts. Accordingly, exemplifications are given therein directed to salts of the alkali metals sodium and potassium. To achieve a rapid response with an antiallergic substance for therapeutic purposes a dosage form is required which can be administered topically to mucous membranes. This in general requires presentation of the drug as a non-irritating solution or dry powder, the solution being preferable due to less difficulty in controlling the dosage when given, for example, as a nasal instillation.

Accordingly, the primary object of the present invention is to provide a water-soluble, stable, therapeutically acceptable form of an antiallergic agent MJ 12175 which can be administered topically. This object as well as other features and advantages of the invention will be readily apparent to those skilled in the art from the disclosure set out below and accompanying claims.

SUMMARY AND DETAILED DESCRIPTION OF THE INVENTION

This invention is concerned with the amine salt comprised of MJ 12175 and N-methyl-D-glucamine in which the acid to base molecular ratio comprises a 1:1 ratio of equivalents of each.

Many conventional pharmaceutically acceptable amine salts of MJ 12175 are not well suited for the present use due to limited solubility, lack of stability, pH ranges differing sufficiently from physiological pH (~7.4) to the extent that irritation of tissue becomes a problem. The following table shows solubility and pH data for various salts of MJ 12175 at room temperature (about 25° C.).

TABLE 1

| | Salts of MJ 12175 | | | |
|---|---|---|---|---|
| | | H2O Solubility (mg/ml) | | |
| Salt No. | Base | in situ | isolated salt | pH |
| 1 | dipotassium[1] | — | 8.9 | 11.22 |
| 2 | N—methyl-D-glucamine | >40 | 12 | 6.4 |
| 3 | arginine | >40 | 5 | 4.7 |
| 4 | glycine | ppt | — | |
| 5 | imidazole | ppt | — | |
| 6 | ethanolamine | ppt | — | |
| 7 | ethylenediamine | ppt | — | |
| 8 | tris(hydroxymethyl) aminomethane | ppt | — | |
| 9 | diethanolamine | >40 | <1 | 6.81 |
| 10 | triethylamine | >40 | — | 4.55 |
| 11 | triethanolamine | >40 | —[2] | 6.42 |
| 12 | N—(2-hydroxyethyl)-morpholine | >40 | — | 6.29 |
| 13 | N—methyldiethanol-amine | >40 | — | 8.08 |
| 14 | tetramethyl-ammonium hydroxide | >40 | — | 9.59 |

[1]In presence of strong base, the proton on the ring nitrogen of MJ 12175 can also be replaced with a cation.
[2]Salt No. 11 could not be purified and solubility of the isolated material was not precisely determined; however, the isolate would not give complete water solubility.

The amine salts of MJ 12175 shown in Table 1 were first prepared in situ by adding the amine to a suspension of MJ 12175 in a quantity of water sufficient to give a 4% aqueous solution of the resulting salt. When a precipitate formed on amine addition indicating relative insolubility, pH was not measured as in the cases of salts 4 through 8 in Table 1. Although solutions were obtained with the other salts formed in situ supersaturation of these solutions appears likely since the four salts (Nos. 2, 3, 9, 11) which were isolated were less than 4% soluble on redissolution. Three of these isolated salts tended to be stable crystalline materials while the fourth (No. 11) remained a non-crystalline tar during attempted purification. The three crystalline salts were the only examples where solid precipitated from the in situ solutions on standing. Of the three crystalline isolated amine salts of MJ 12175, the glucamine salt best meets the water solubility and pH criteria. Further development work with the glucamine salt has demonstrated the stability of its aqueous solutions on extended storage. As examination of Table 1 demonstrates, suitability of the various amine salts on the basis of water solubility and pH is not predictable beforehand.

Preparation of the glucamine salt of MJ 12175 comprises suspending MJ 12175 in alcohol and treating the suspension with a hot alcoholic solution of the base, N-methyl-D-glucamine. Continued stirring and filtration yields the pure salt product containing an acid to base ratio of 1:1.

In addition to the aforementioned desired solubility, physical suitability and pH properties exhibited by the instant salt, its other physical properties are such that no compatibility problems exist in formulating the salt into buffered solutions intended for topical administration.

A preferred solution for topical administration is a preserved aqueous solution, buffered within the pH range of 5.0 to 8.0, containing an MJ 12175 glucamine salt concentration of 0.2 to 1.2% weight to volume. This solution may also contain preservatives such as methyl paraben, propyl paraben, phenylethyl alcohol, or benzyl alcohol; buffers such as citrate, phosphate, acetate; chelating agents such as ethylenediamine, tetraacetic acid salts, bis-(2-hydroxyethyl)glycine, and tartaric acid; and antioxidants such as sodium bisulfite, ascorbic acid, and cysteine hydrochloride. These pharmaceutical additives are frequently used in products of this type.

The N-methyl-D-glucamine of MJ 12175 salt may also be administered using other dosage forms. This salt can be dissolved or suspended in a halocarbon or hydrocarbon propellant system and packaged in a metered dose aerosol container. Cosolvents or surfactants and suspending agents may also be included in this dosage form. The salt can also be administered as a powder for insufflation, consisting of a blend of inert ingredients admixed with an appropriate amount of the glucamine salt of appropriate particle size, administered by a powder insufflation device.

DESCRIPTION OF SPECIFIC EMBODIMENTS

The following non-limiting examples illustrate the invention.

EXAMPLE 1

Preparation of MJ 12175 Carboxylic Acid
3,4-Dihydro-5-methyl-6-(2-methylpropyl)-4-oxothieno[2,3-d]pyrimidine-2-carboxylic Acid A solution of 37.6 g (0.01 mole) dipotassium 3,4-dihydro-5-methyl-6-(2-methylpropyl)-4-oxothieno[2,3-d]pyrimidine-2-carboxylate hydrate in 1.1 liter water at 40° C. was treated with 5 g activated charcoal and filtered. The filtrate was added with stirring over a 3 hr period to a solution of 21 ml (0.25 mole) 37% hydrochloric acid in 0.5 liter water maintained at 35°-38° C. The mixture was stirred for an additional 2 hr, and then the solid was collected on a filter, rinsed with water and air-dried to give 26.5 g of off-white product, m.p. 140.5°-141.5° C. (dec.). The product was slurried with 250 ml methanol to remove a slight yellow color and then filtered and air-dried. The IR and NMR were consistent for the assigned structure of MJ 12175.

Anal. Calcd. for $C_{12}H_{14}N_2O_3S \cdot H_2O$: C, 50.69; H, 5.67; N, 9.85; $H_2O$, 6.34. Found: C, 50.87; H, 5.65; N, 10.00; $H_2O$, 5.19.

The dipotassium salt of MJ 12175 utilized in the above example can be obtained according to the procedure outlined in the earlier cited Temple patents, specifically, Procedure 97 in U.S. Pat. No. 4,159,377 incorporated herein by reference.

EXAMPLE 2

Preparation of MJ 12175 Glucamine Salt
3,4-Dihydro-5-methyl-6-(2-methylpropyl)-4-oxothieno[2,3-d]pyrimidine-2-carboxylic Acid
N-methyl-D-glucamine Salt MJ 12175, the product of Example 1 shown above, was stirred (48.2 g, 0.18 mole) in 1.5 liter methanol at 25° C. A solution of 35.3 g (0.18 mole) N-methyl-D-glucamine in 300 ml boiling methanol was added all at once with vigorous stirring. Nearly all of the solid dissolved before a thick precipitate began to form. This mixture was stirred 2 hr and then chilled to 10° C. The solid was collected on a filter, rinsed with additional methanol and air-dried. The white solid weighed 75.5 g (90.4% of theory), m.p. 180.5°-182° C. (with bubbling).

Anal. Calcd. for $C_{12}H_{14}N_2O_3S \cdot C_7H_{17}NO_5$; C, 49.45; H, 6.77; N, 9.10; S, 6.95. Found: C, 49.47; H, 6.84; N, 9.06; S, 6.98.

NMR (DMSO-$d_6$): Chemical shift (number protons, multiplicity)-0.94 (6,d); 1.85 (1,m); 2.40 (3,S); 2.60 (3,s); 2.64 (2,d); 3.10 (2,m); 3.52 (4,m); 3.71 (1,m); 3.97 (1,m); 6.00 (8,bs).

IR (KBr): 1080, 1370, 1470, 1570, 1635, 1670, 2900, 2930, 2960, 3260, 3370, and 3460 $cm^{-1}$.

EXAMPLE 3

Solution For Topical Nasal Administration

The MJ 12175 glucamine salt of the instant invention is preferably administered as a preserved buffered aqueous solution. The composition of some typical operable solutions of MJ 12175 glucamine salt are shown in Table 2.

TABLE 2

| COMPOSITIONS OF MJ 12175 GLUCAMINE SALT SOLUTIONS | | | | |
|---|---|---|---|---|
| Ingredients | Percent (W/V) | | | |
| MJ 12175-Glucamine Salt | 1.00 | 0.50 | 0.25 | 0.0 |
| Potassium Phosphate, Dibasic | 0.43 | 0.43 | 0.43 | 0.43 |
| Propylene Glycol | 10.0 | 10.0 | 10.0 | 10.0 |
| Hydrochloric Acid, to adjust pH to 7.5 | | | | |
| Purified Water, V.H.R., q.s. | 100 | 100 | 100 | 100 |

What is claimed is:

1. The N-methyl-D-glucamine salt of 3,4-dihydro-5-methyl-6-(2-methylpropyl)-4-oxothienyl[2,3-d]pyrimidine-2-carboxylic acid.

2. The salt of claim 1 wherein the molecular ratio of N-methyl-D-glucamine to said acid is 1:1.

3. The salt of claim 1 in dilute solution suitable for nasal instillation comprising a liquid pharmaceutical carrier containing an effective immediate hypersensitivity reaction inhibiting concentration of said salt.

4. The salt of claim 1 in a stabilized, buffered, dilute aqueous solution containing from 0.2 to 1.2% (W/V) of said salt for nasal application.

* * * * *